US012654034B2

(12) United States Patent
Cossu et al.

(10) Patent No.: US 12,654,034 B2
(45) Date of Patent: Jun. 16, 2026

(54) METHOD OF IDENTIFYING AN ISOCENTER

(71) Applicant: Elekta Limited, Crawley (GB)

(72) Inventors: Antonio Cossu, Crawley (GB);
Roberto Anselmi, Crawley (GB);
Antonio Giovanni Vescovi, Crawley
(GB)

(73) Assignee: Elekta Limited, Crawley (GB)

( * ) Notice: Subject to any disclaimer, the term of this
patent is extended or adjusted under 35
U.S.C. 154(b) by 215 days.

(21) Appl. No.: 18/546,545

(22) PCT Filed: Feb. 16, 2022

(86) PCT No.: PCT/EP2022/053853
§ 371 (c)(1),
(2) Date: Aug. 15, 2023

(87) PCT Pub. No.: WO2022/175347
PCT Pub. Date: Aug. 25, 2022

(65) Prior Publication Data
US 2024/0173573 A1      May 30, 2024

(30) Foreign Application Priority Data
Feb. 16, 2021    (GB) ...................................... 2102125

(51) Int. Cl.
*A61N 5/10*          (2006.01)
(52) U.S. Cl.
CPC ......... *A61N 5/1075* (2013.01); *A61N 5/1081*
(2013.01); *A61N 2005/1076* (2013.01)

(58) Field of Classification Search
CPC ................ A61N 5/1075; A61N 5/1081; A61N
2005/1076
See application file for complete search history.

(56) References Cited

U.S. PATENT DOCUMENTS

2002/0133175 A1*  9/2002  Carson ................... A61B 90/10
606/130
2005/0058237 A1*  3/2005  Morf .................... A61N 5/1048
378/4

(Continued)

FOREIGN PATENT DOCUMENTS

EP            3639892 A1      4/2020
WO          2020209667          10/2020
WO      WO-2020209667 A1 * 10/2020  ............... A61B 6/58

OTHER PUBLICATIONS

"International Application Serial No. PCT/EP2022/053853, Inter-
national Search Report dated May 23, 2022", (May 23, 2022), 4 pgs.

(Continued)

*Primary Examiner* — Blake C Riddick
(74) *Attorney, Agent, or Firm* — Schwegman Lundberg &
Woessner, P.A.

(57)          ABSTRACT
There is herein provided a method of identifying an isocen-
tre of a radiotherapy apparatus. The method includes cap-
turing illumination of respective dummy point images at
rotational positions of a component of the radiotherapy
apparatus at an image capture device mounted on the
radiotherapy apparatus and deriving the isocentre from the
captured dummy point images.

17 Claims, 9 Drawing Sheets

(56) References Cited

U.S. PATENT DOCUMENTS

| | | | | |
|---|---|---|---|---|
| 2007/0221869 A1* | 9/2007 | Song | A61N 5/10 | 378/65 |
| 2009/0238338 A1 | 9/2009 | Long et al. | | |
| 2010/0271477 A1* | 10/2010 | Farina | B05B 12/004 | 348/135 |
| 2012/0076269 A1* | 3/2012 | Roberts | A61N 5/1049 | 378/65 |
| 2013/0064346 A1* | 3/2013 | Ferren | A61B 6/51 | 378/62 |
| 2013/0121457 A1* | 5/2013 | Maltz | A61B 6/032 | 378/4 |
| 2013/0237811 A1* | 9/2013 | Mihailescu | G01S 17/66 | 600/407 |
| 2015/0080634 A1* | 3/2015 | Huber | A61B 90/39 | 600/1 |
| 2015/0085993 A1* | 3/2015 | Scheib | A61N 5/1071 | 378/207 |
| 2015/0343239 A1 | 12/2015 | Liu et al. | | |
| 2015/0352375 A1* | 12/2015 | Chen | A61N 5/1049 | 600/1 |
| 2016/0114190 A1* | 4/2016 | Brown | A61B 6/584 | 378/205 |
| 2016/0114191 A1* | 4/2016 | Sankey | A61N 5/1049 | 378/65 |
| 2017/0046856 A1* | 2/2017 | Hirai | G06T 11/003 | |
| 2017/0080254 A1* | 3/2017 | Scheib | A61N 5/1049 | |
| 2017/0106213 A1* | 4/2017 | Lee | A61B 6/032 | |
| 2017/0113067 A1* | 4/2017 | Lee | A61N 5/1037 | |
| 2017/0128029 A1* | 5/2017 | Penfold | A61B 6/4258 | |
| 2017/0128747 A1* | 5/2017 | Bennett | G21K 1/08 | |
| 2017/0186146 A1* | 6/2017 | Raniwala | H04N 23/60 | |
| 2017/0189722 A1* | 7/2017 | Reno | G21K 1/08 | |
| 2017/0196641 A1* | 7/2017 | Jagga | A61B 90/10 | |
| 2017/0197097 A1* | 7/2017 | Michaud | A61N 5/1069 | |
| 2017/0197099 A1* | 7/2017 | Ruebel | A61N 5/1049 | |
| 2018/0021598 A1* | 1/2018 | Bergfjord | A61B 6/4435 | 600/427 |
| 2018/0133508 A1 | 5/2018 | Pearce et al. | | |
| 2019/0001156 A1* | 1/2019 | Tulik | A61N 5/1081 | |
| 2019/0134428 A1* | 5/2019 | Gersh | G01T 1/2921 | |
| 2019/0357986 A1* | 11/2019 | Morgan | A61B 34/30 | |
| 2020/0090371 A1* | 3/2020 | Hu | H04N 17/002 | |
| 2020/0114173 A1* | 4/2020 | Little | A61B 90/39 | |
| 2020/0268339 A1* | 8/2020 | Hao | A61B 6/544 | |
| 2021/0370100 A1* | 12/2021 | Yock | A61N 5/1075 | |

OTHER PUBLICATIONS

"International Application Serial No. PCT/EP2022/053853, Written Opinion dated May 23, 2022", (May 23, 2022), 5 pgs.

"United Kingdom Application Serial No. 2102125.8, Examination Report dated Jul. 16, 2021", (Jul. 16, 2021), 7 pgs.

Cheon, Wonjoong, et al., "Quality assurance of isocentres for passive proton beam nozzles using motion capture cameras", Physica Medica 70, (Feb. 1, 2020), pp. 139-144.

"European Application No. 22 707 074.5, Office Action dated Jul. 15, 2025", (Jul. 15, 2025), 3 pgs.

* cited by examiner

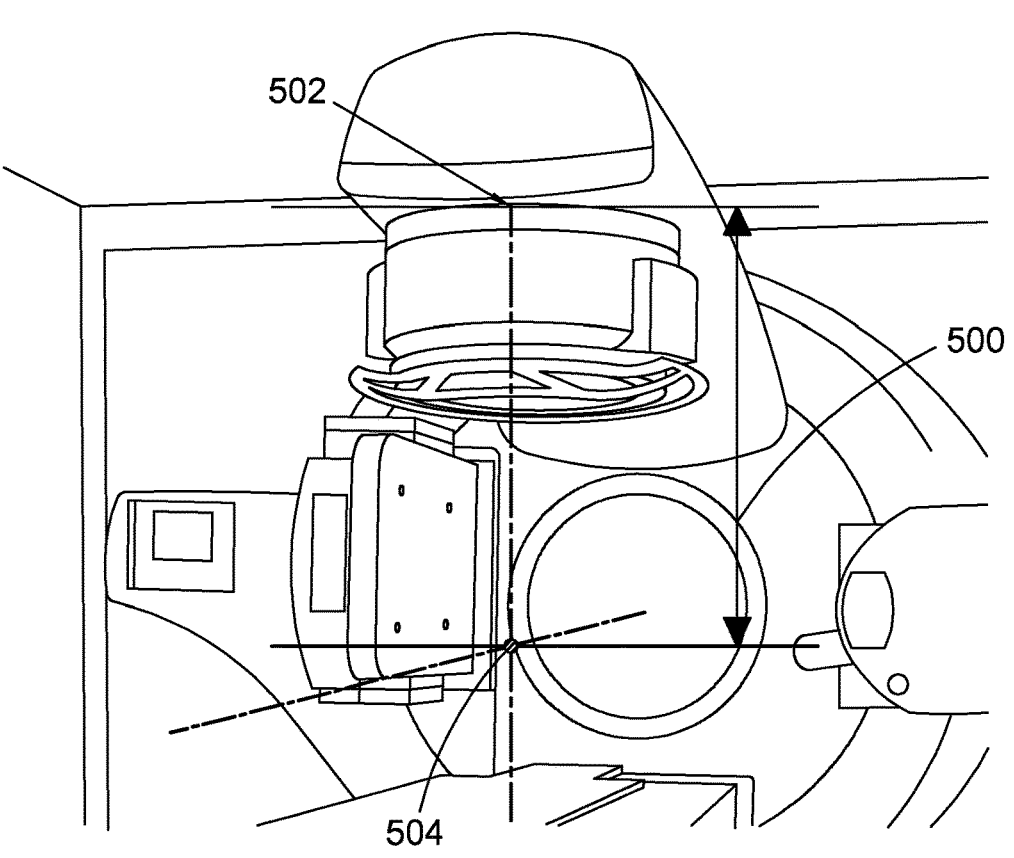
Fig. 5
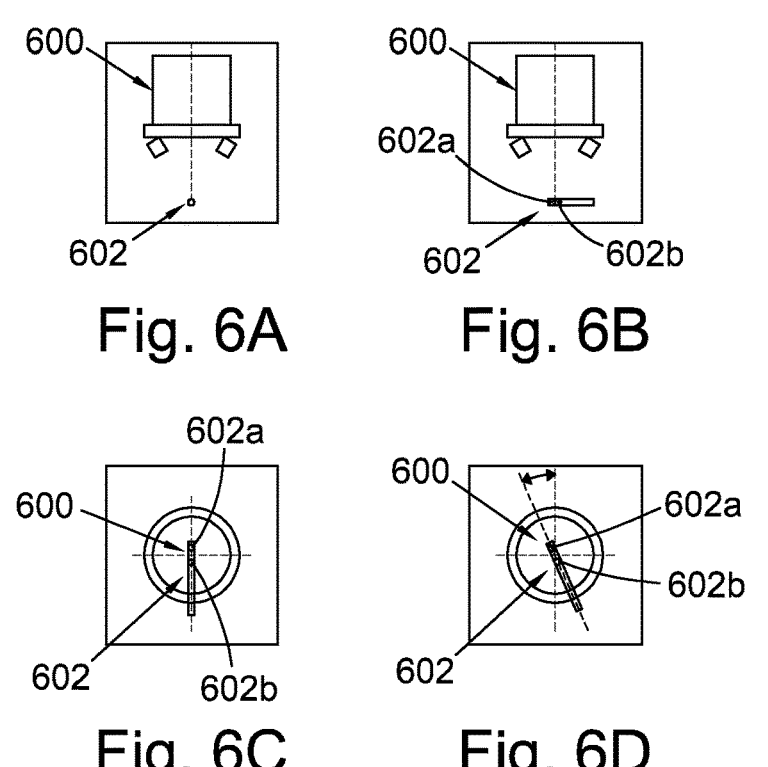
Fig. 6A          Fig. 6B
Fig. 6C          Fig. 6D

604a    604b

700 — 1. Head Rotation analysis

702 — 2. Gantry Drum Rotation analysis

704 — 3. Couch Rotation analysis

METHOD OF IDENTIFYING AN ISOCENTER

PRIORITY APPLICATIONS

This application is a U.S. National Stage Filing under 35 U.S.C. § 371 from International Application No. PCT/EP2022/053853, filed on Feb. 16, 2022, and published as WO2022/175347 on Aug. 25, 2022, which claims the benefit of priority to British Application No. 2102125.8, filed on Feb. 16, 2021; the benefit of priority of each of which is hereby claimed herein, and which applications and publication are hereby incorporated herein by reference in their entireties.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour. Additionally, magnetic resonance (MR) imaging can be performed before and during treatment. A patient lies on a patient support surface and patient movement is minimised to ensure the treatment area remains stationary.

The radiotherapy is applied to a predetermined treatment volume, and this is defined as the isocentre. The isocentre must be determined in a calibration phase in order that machine variations can be taken into account, especially as the level of beam precision is such that isocentre accuracy has a non-negligible effect on the treatment. Conventional processes use the Winston Lutz test according to which the treatment beam position is measured through various operational positions of the apparatus. However, this means that the test can only be performed at late stages of the installation process, when the machine is fully functioning and can irradiate. Furthermore, the existing tests depend on the good mechanical set up of the machine, however this needs to be ensured during production and early stages of the installation process at which stage measurement and calibration cannot be performed.

The invention is set out in the claims.

SUMMARY

Specific embodiments are now described, by way of example only, with reference to the drawings, in which:

FIG. 5 depicts source-axis distance derivation according to an embodiment; and

FIGS. 6A to 6E depict a dual reference marker apparatus according to an embodiment;

OVERVIEW

In overview, the invention relates to methods and tools providing an estimate of the isocentre accuracy using non-radiating measurements. For example, the isocentre of the radiotherapy apparatus can be identified by capturing respect dummy point images, for example of a BB phantom or other point fixed relative to a room housing the radiotherapy apparatus, at various rotation positions of a component of the radiotherapy apparatus such as the gantry, patient support surface and/or radiation beam shaping collimator. The image capture device can be a digital camera or other suitable device mounted to the radiotherapy apparatus. The isocentre can then be derived from the captured dummy point images, for example by extrapolating an effective centre. As a result, fine measurement of the isocentre accuracy can be obtained by an optical method not requiring irradiation, providing results comparable to those obtained by measurements in a radiation field, but at far earlier stages when generation of a radiation beam may not yet be possible. In optional embodiments, by using two or more image capture devices additional 3D information can be obtained permitting yet further accuracy. Accordingly, machine set up and calibration can be improved at a much earlier stage and with efficiency and accuracy significantly enhanced.

DETAILED DESCRIPTION

Figure 1:
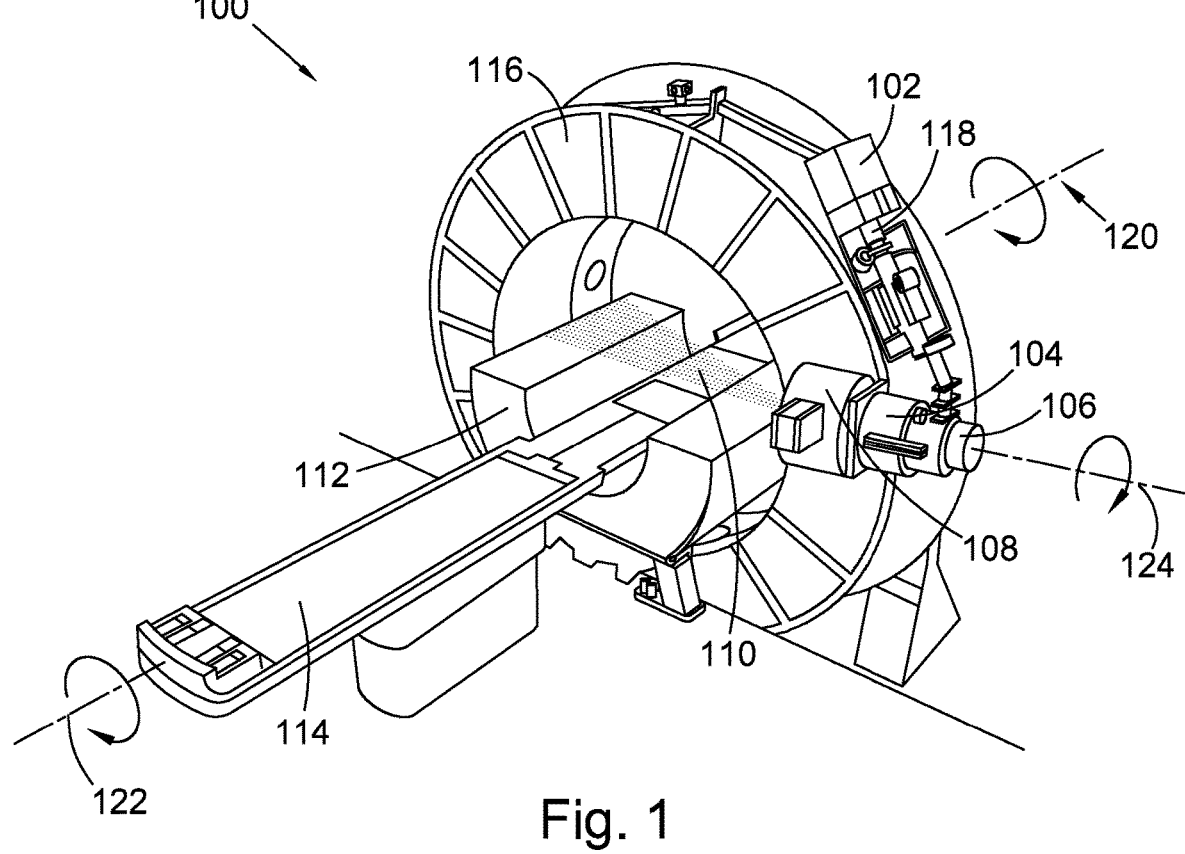
FIG. 1 depicts a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device may comprise both MR imaging apparatus 112 and radiotherapy (RT) apparatus which may comprise a linac device. The MR imaging apparatus is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital. The skilled reader will be familiar with suitable MR and linac devices such that detailed description is not required here.

The MR-linac device depicted in FIG. 1 comprises a source of radiofrequency waves 102, a waveguide 104a source of radiation 106, a collimator 108 such as a multi-leaf collimator configured to collimate and shape the beam 110, MR imaging apparatus 112, and a patient support surface 114. In use the device would also comprise a housing (not shown) which, together with the ring-shaped gantry defines a bore. The moveable support surface 114 can be used to move a patient, or other subject, into the bore when an MR scan and/or when radiotherapy is to commence. The MR imaging apparatus 112, RT apparatus 120, and a subject support surface actuator are communicatively coupled to a controller or processor. The controller is also communicatively coupled to a memory device comprising computer-executable instructions which may be executed by the controller.

The radiation source 106 may comprise a beam generation system. For a linac, the beam generation system may comprise a source of RF energy 102, an electron gun, a circulator 118 and a waveguide 104. The radiation source is attached to the rotatable gantry 116 so as to rotate with the gantry 116. In this way, the radiation source 106 is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source of radiation 106 is configured to direct the beam 110 of therapeutic radiation toward a patient positioned on the patient support surface 114. The source of radiation 106 may comprise a heavy metal target toward which the high energy electrons exiting the waveguide are directed. When the electrons strike the target, X-rays are produced and collimated by collimator 108.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms "subject" and "patient" are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the subject support surface. The controller is communicatively coupled to a memory, i.e. a computer readable medium.

The linac device also comprises several other components and systems as will be understood by the skilled person. For example, in order to ensure the linac does not leak radiation, appropriate shielding is also provided.

As indicated above, the isocentre requires careful definition and identification in the radiotherapy apparatus in order to ensure that treatment is delivered to the correct region. Referring to FIG. 1, once again, it can be seen that there are multiple degrees of freedom. In particular the gantry rotates about an axis 120, the patient support surface 114 rotates around an axis 122 parallel to the axis 120 and the collimator 108 rotates around an axis 124 which is perpendicular to the axis 120.

Multiple definitions exist in relation to the definition of "isocentre" and, additionally, some are based on incorrect assumptions such that the axes of rotation will coincide at a point. In fact, owing to mechanical tolerances and physical aspects such as sag of the gantry in view of its significant weight, the isocentre can be highly variable both in static and dynamic circumstances. Zhang et al in the paper "What do you mean when we talk about the linac isocentre?" International Journal of Medical Physics, Clinical Engineering and Radiation Oncology, 2015, 4, 233-242 provide the following definitions for the isocentre, distinguishing between the mechanical isocentre and the radiation isocentre:

The mechanical isocentre is considered to be the centre of the smallest sphere that intercepts the mechanical axis of rotation of the gantry, collimator and patient support surface for different combinations of angles of rotation of each.

The radiation isocentre is considered to be the centre of the smallest sphere that intercepts all the central radiation beam rays directed from a different combination of gantry and collimator rotation angles.

Currently quality assurance guidelines recommend measuring both mechanical and the radiation isocentres and verifying their coincidence as being within a certain tolerance. However, the mechanical and radiation isocentres may differ; the mechanical isocentre is a geometrical rigid body concept, however in the case of the radiation isocentre the central radiation beam ray can deviate from the rotation axis for various reasons such as beam steering.

The know Winston Lutz method described at, for example, "Evaluation of Different Winston-Lutz Analyses", S. Alzaidi et al uses a ball bearing phantom fixed relative to a room housing the radiotherapy apparatus, and rotates the radiotherapy apparatus components including gantry, collimator and/or patient support surface whilst generating a treatment beam. Movement of the ball bearing phantom image captured by the treatment beam detector is obtained for multiple rotational positions in order to identify an isocentre corrected for rotational deviation. As indicated above, the Winston Lutz method requires the apparatus to be fully operational to the point of generation of an irradiation beam. Furthermore, it is based on planar, two dimensional acquisitions according to which the approximation of the preferred isocentre definition is applied considering the radiation isocentre as the smallest 2D circle on a plane at a fixed source-axis distance (nominal SPD) from the beam source intercepting all the central beam rays. As variation in the delivered dose is less sensitive to error along the beam path as opposed to in the plane orthogonal to beam path, this approximation can in some instances be acceptable, however additional accuracy may in some instances be desirable.

A method of identifying isocentre according to a first embodiment of the invention will now be described.

Figure 2:
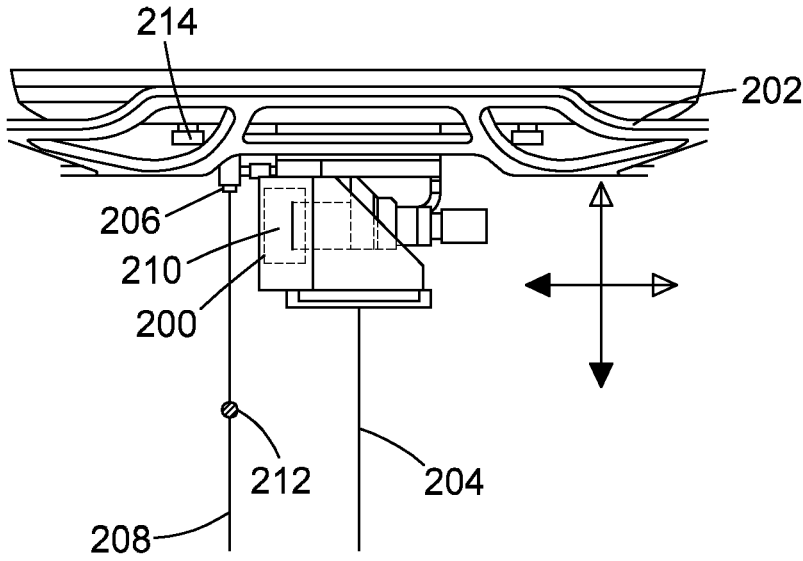
FIG. 2 depicts an optical isocentre capture apparatus according to an embodiment.

Referring to FIG. 2 an isocentre identification method and system according to the claimed approach can be understood in more detail. In particular, the collimator 200 is mounted to a gantry 202 and has a beam axis 204. A digital camera and optics 206 are mounted to the collimator and linac head in such a way that the optical axis 208 is parallel to the beam axis 204. A ring illuminator or other suitable illumination device 210 is provided parallel to or co-axial with the camera optics. This is used to light a reference marker 212 such as a sphere fitted on a ball bearing phantom which is located in and fixed in a frame of reference relative to which the radiotherapy apparatus components rotate, for example the room housing the radiotherapy apparatus.

Figure 3:
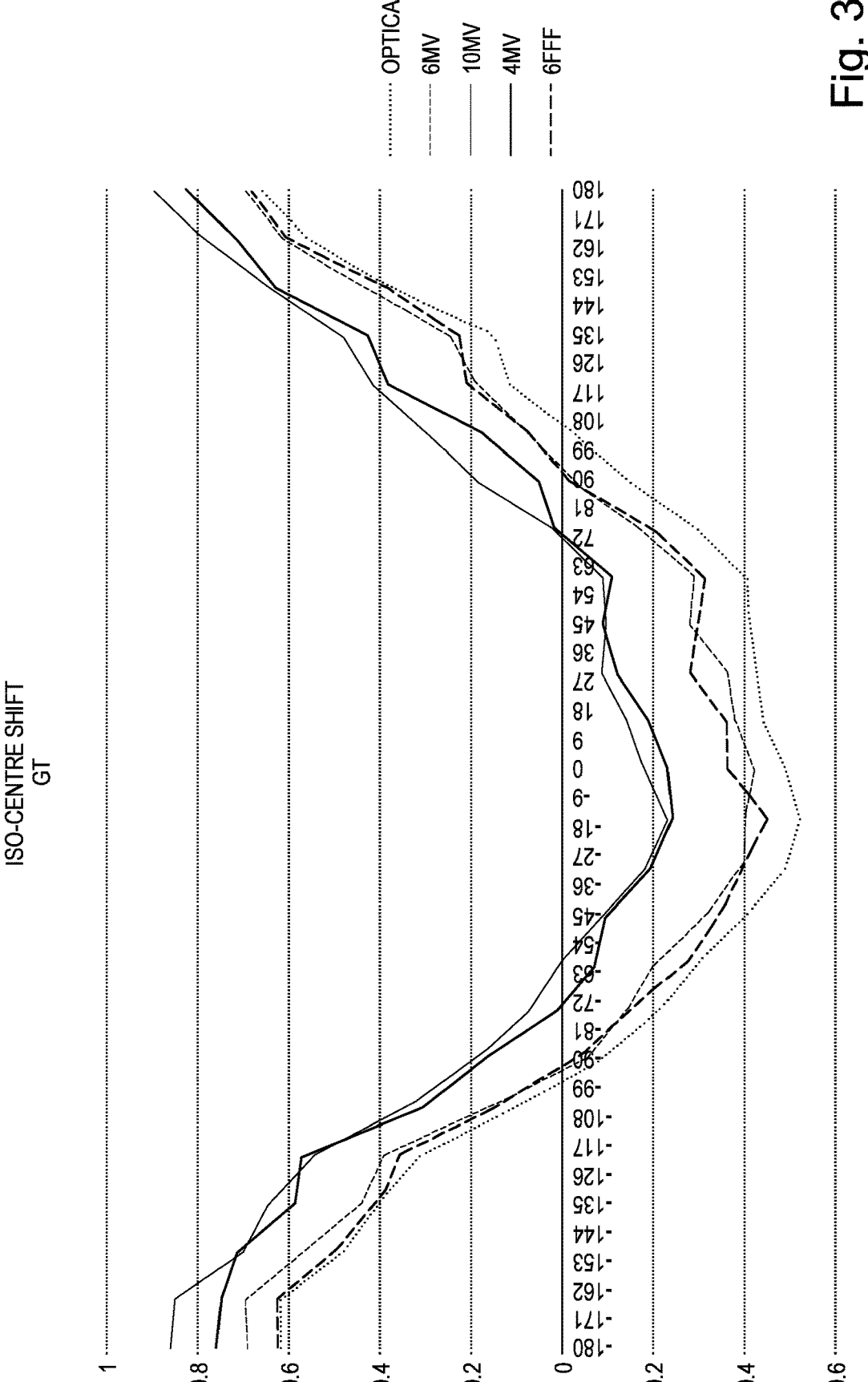
FIG. 3 depicts optical isocentre calibration data according to an embodiment.

In operation, and as discussed in more detail below, images obtained by the camera are used to detect isocentre deviations occurring during movement of the radiotherapy apparatus components including the gantry 202, collimator 200 and/or patient support system (not shown). In particular, and as discussed in more detail below, by observing the position of the reference marker such as the ball bearing phantom 212, variations in the isocentre along directions orthogonal to the beam axis can be derived in some embodiments from the captured image. Through appropriate coordinate transformations, the measurement can be associated with the respective configuration of the radiotherapy apparatus, namely the position of the gantry, collimator and/or patient support system, and the results of the measurements can be analysed to identify the isocentre and/or evaluate the isocentre accuracy. FIG. 3 for example shows an example of the identification of isocentre deviation as a function of gantry angle between +180° and −180°.

The nature of the reference marker can vary—it can for example be a passive ball bearing sphere as described above or an active reference marker. In cases of early measurement or calibration, the machine may not yet configured to provide a gantry position readout in which case an inclinometer 214 can be provided to detect the position of the gantry 202. As a result, the rotational data can be captured for calibration and measurement purposes.

The active reference marker can, for example, comprise a light source such as an IR (infrared) LED at the marker location for example provided in conjunction with a semi-opaque white enclosure. The location of the active marker will be detected and used for calibration purposes in the same manner as the passive marker but without the requirement for additional illumination in some embodiments. It will be noted that passive or active markers can be used interchangeably in all of the embodiments described herein.

The manner of calibration will now be described in more detail. Dealing firstly with calibration of the collimator rotational axis, the position of the reference marker 212 is captured at different angles of rotation of the collimator head, and, using a least squares fit technique, a centre to the locus of the detected positions is identified as the new origin. As a result, the models find the centre and radius of the circle that best fits the acquired points using a least square minimisation of the residuals between the unknown circle and the acquired points for example using a Moore-Penrose pseudo-inverse matrix approach of the type known to the skilled reader. In an approximation, tilt of the head axis is considered to be small or null such that the determination to the centre is performed in the XY plane and the Z position of the point is not used. As discussed in more detail below, however, additional data can be incorporated to obtain a three-dimensional point as appropriate, and in embodiments the calibration tool provides for availability of the Z position in the software analysis tool as well.

Solving the problem as described in the preceding paragraph, the center $c=(c_x, c_y)$ and radius r fitted from the set of M acquired points $p_i=(p_{i,x}; p_{i,y})$ in the 2-dim plane are:

$$\begin{cases} c_x = \frac{1}{2}y_1 \\ c_y = \frac{1}{2}y_2 \\ r = \sqrt{y_3 + \frac{1}{4}y_1^2 + \frac{1}{4}y_2^2} \end{cases}$$

Where y is the vector the solves the linear system:

$$y = B^+ \cdot d$$

With:

$$y = \begin{bmatrix} y_1 \\ y_2 \\ y_3 \end{bmatrix} \qquad B^+ = \left(B^T \cdot B\right)^{-1} \cdot B^T$$

$$d = \begin{bmatrix} p_{1,x}^2 + p_{1,y}^2 \\ ... \\ p_{M,x}^2 + p_{M,y}^2 \end{bmatrix} \quad B = \begin{bmatrix} p_{1,x} & p_{1,y} & 1 \\ ... & ... & ... \\ p_{M,x} & p_{M,y} & 1 \end{bmatrix}$$

Once the best circle is found, the maximum, average and standard deviation distances can be used as an estimation of the quality of the fit:

$$\begin{cases} d_{max} = \max_i \left( \left| \sqrt{(c_x - p_{i,x})^2 + (c_y - p_{i,y})^2} - r \right| \right) \\ d_{avg} = \dfrac{\sum_{i=1}^{M} \left( \left| \sqrt{(c_x - p_{i,x})^2 + (c_y - p_{i,y})^2} - r \right| \right)}{M} \\ \sigma_d = \sqrt{\dfrac{\sum_{i=1}^{M} \left( \left| \sqrt{(c_x - p_{i,x})^2 + (c_y - p_{i,y})^2} - r \right| - d_{avg} \right)^2}{N - 1}} \end{cases}$$

The analytical description of a point p laying on a circle with radius r and center c is (bold means vector):

$$\|c - p\|^2 - r^2 = 0$$

This model finds in N dimensions the values of center and radius of the best fitting circle minimizing the sum of the squares of the residuals between M points $p_i$ and the unknown circle as follows:

$$\min_{c,r} \sum_{i=1}^{M} (\varepsilon_i(c, r))^2$$

Where the residual between each point and the circle is defined as follows:

$$\varepsilon_i(c, r) = \|c - p_i\|^2 - r^2$$

Note that the "total least square model" defines the residual as the distance between the point and the nearest point in the circle $\varepsilon_i(c,r)=|\|c-p_i\|-r|$. This definition results in a non-linear minimization problem that is heavier from a computational viewpoint and, since guarantees only to find a local minimum, is highly dependent on the choice of the starting point of the minimization process.

However, the current approach recognizes that although at at first sight this problem is non-linear, writing the residual in the form:

$$\varepsilon_i(c, r) = c^T \cdot c - 2 \cdot c^T \cdot p_i + p_i^T \cdot p_i - r^2$$

allows the linearity to be removed by making a (non-linear) transformation of variables:

$$y = \begin{bmatrix} 2c \\ r^2 - c^T \cdot c \end{bmatrix}; b_i = \begin{bmatrix} p_i \\ 1 \end{bmatrix}$$

then the residual becomes:

$$\varepsilon_i(y) = p_i^T \cdot p_i - b_i^T \cdot y$$

and the minimization problem becomes:

$$\min_y \sum_{i=1}^{M} (p_i^T \cdot p_i - b_i^T \cdot y)^2$$

Finally, defining the matrix B and the vector D as follows:

$$B = \begin{bmatrix} b_1^T \\ \cdots \\ b_M^T \end{bmatrix} = \begin{bmatrix} p_{1,1} & \cdots & p_{1,N} & 1 \\ \cdots & \cdots & \cdots & \cdots \\ p_{M,1} & \cdots & p_{M,N} & 1 \end{bmatrix}; d = \begin{bmatrix} \|p_1\|^2 \\ \cdots \\ \|p_M\|^2 \end{bmatrix}$$

or in a more compact form:

$$\min_y \|B \cdot y - d\|^2$$

which is equivalent of solving the linear system:

$$B \cdot y = d$$

since B is a rectangular matrix M×N (N is the dimension of the space where we are performing the minimization) the system is over-determined and, if at least N+1 columns in the matrix B are linearly independent, has a unique solution.

The solution can be found calculating the Moore-Penrose pseudo-inverse matrix $B^+$:

$$B^+ = (B^T \cdot B)^{-1} \cdot B^T$$

and solving the linear system:

$$y = B^+ \cdot d$$

obtaining the following values for center x and radius r:

$$\begin{cases} c_j = \frac{1}{2} y_j \\ r = \sqrt{y_{N+1} + c^T \cdot c} \end{cases}$$

Once the center c of the best circle is found, the maximum, average and standard deviation distances of the M points $p_i$ can be calculated to be used as estimators of the fit quality:

$$\begin{cases} d_{max} = \max_i(\|\|c - p_i\| - r\|) \\ d_{avg} = \dfrac{\sum_{i=1}^{M}(\|\|c - p_i\| - r\|)}{M} \\ \sigma_d = \sqrt{\dfrac{\sum_{i=1}^{M}(\|\|c - p_i\| - r\| - d_{avg})^2}{M-1}} \end{cases}$$

As a result, the axis of rotation of the collimator can be determined using optical techniques permitting improved mounting and calibration. As discussed above, this can be combined with determination of other axes and parameters by optical techniques in order to find the isocentre without requiring activation of the radiation source.

In addition, therefore, it is further necessary to find the gantry isocentre which can be used in conjunction with the collimator isocentre and, as required, the patient support surface isocentre to obtain the machine isocentre. Furthermore, once the isocentre is found, the maximum, average and standard deviation distances of the discovered points can be calculated to use as estimator of the quality of the calibration.

In a two-dimensional average centre model (where a single camera is used), the calibration method uses a series of observed reference points for different gantry angles, preferably at least four gantry angles, and calculates the average position of the isocentre for the given points. Hence the position of the isocentre in the relevant coordinate system is provided that best fits the data points.

In order to use the same type of information available for the calibration in the radiation field, this method uses only the 2D components in the plane orthogonal to the beam direction of each acquired point.

The points are acquired for a full rotation of the gantry and at constant steps.

Preferably if the set is composed of two or more full rotations (e.g. CW and CCW) they must be acquired at the same gantry angles (with −180° and 180° considered as same angle).

The j-th 2D component $$Q_j^b(x_j^b, y_j^b)$$

of the point $$P_j^b(x_j^b, y_j^b, z_j^b)$$

acquired in the beam system at gantry angle $\theta_j$, is transformed into $P_j(x_j, y_j, z_j)$ in IEC 61217 coordinate system as follows:

$$\begin{cases} x_j = x_j^b \cdot \cos\theta_j \\ y_j = y_j^b \\ z_j = x_j^b \cdot \sin\theta_j \end{cases}$$

The best isocenter $C(x_c, y_c, z_c)$ is computed as the average position of the $P_j(x_j, y_j, z_j)$ in the relevant coordinate system for example as defined in the IEC 61217 standard "Radiotherapy equipment, coordinates, movements and scales":

$$\begin{cases} x_c = \dfrac{\sum_{j=1}^N x_j}{N} \\ y_c = \dfrac{\sum_{j=1}^N y_j}{N} \\ z_c = \dfrac{\sum_{j=1}^N z_j}{N} \end{cases} \rightarrow \begin{cases} x_c = \dfrac{\sum_{j=1}^N x_j^b \cdot \cos\theta_j}{N} \\ y_c = \dfrac{\sum_{j=1}^N y_j^b}{N} \\ z_c = \dfrac{\sum_{j=1}^N x_j^b \cdot \sin\theta_j}{N} \end{cases}$$

Once the best isocenter is found, the maximum, average and standard deviation distances of the N points $$Q_j^b(x_j^b, y_j^b)$$

can be calculated to be used as estimator of the quality of the calibration.

For each point $$Q_j^b(x_j^b, y_j^b),$$

the 2D position in respect to the best isocenter is calculated as:

$$\begin{cases} \Delta x_j = (x_j - x_c) \cdot \cos\theta_j + (z_j - z_c) \cdot \sin\theta_j \\ \Delta y_j = y_j - y_c \end{cases} \rightarrow$$

$$\begin{cases} \Delta x_j = (x_j^b \cdot \cos\theta_j - x_c) \cdot \cos\theta_j + (x_j^b \cdot \sin\theta_j - z_c) \cdot \sin\theta_j \\ \Delta y_j = y_{j_j}^b - y_c \end{cases}$$

Therefore, the 2D distance from the best isocenter of each j-th point $$Q_j^b(x_j^b, y_j^b)$$

is:

$$d_j = \sqrt{\Delta x_j^2 + \Delta y_j^2}$$

Finally, the maximum, average and standard deviation distances are calculated as:

$$\begin{cases} d_{max} = \max_j (d_j) \\ d_{avg} = \dfrac{\sum_{j=1}^N (d_j)}{N} \\ \sigma_d = \sqrt{\dfrac{\sum_{j=1}^N (d_j - d_{avg})^2}{N-1}} \end{cases}$$

If the measured data set contains for example only 4 points acquired at gantry $-180°$, $-90°$, $0°$ and $180°$, this model is equivalent to the RIT procedure in a radiation field. In this case the above model description can be rewritten with a more intuitive notation.

The set of acquired points in beam system is:

$$\begin{cases} P_{-180}^b(x_{-180}^b, y_{-180}^b, z_{-180}^b) \\ P_{-90}^b(x_{-90}^b, y_{-90}^b, z_{-90}^b) \\ P_0^b(x_0^b, y_0^b, z_0^b) \\ P_{90}^b(x_{90}^b, y_{90}^b, z_{90}^b) \end{cases}$$

The best isocenter $C(x_c, y_c, z_c)$ is, in the IEC 61217 coordinate system:

$$\begin{cases} x_c = \dfrac{x_0^b - x_{-180}^b}{2} \\ y_c = \dfrac{y_{-180}^b + y_{-90}^b + y_0^b + y_{90}^b}{4} \\ z_c = \dfrac{x_{90}^b - x_{-90}^b}{2} \end{cases}$$

The four 2D distances from the best isocenter are:

$$\begin{cases} d_{-180} = \sqrt{(x_{-180}^b + x_c)^2 + (y_{-180}^b - y_c)^2} \\ d_{-90} = \sqrt{(x_{-90}^b + z_c)^2 + (y_{-90}^b - y_c)^2} \\ d_0 = \sqrt{(x_0^b - x_c)^2 + (y_0^b - y_c)^2} \\ d_{90} = \sqrt{(x_{90}^b - z_c)^2 + (y_{90}^b - y_c)^2} \end{cases}$$

And maximum, average and standard deviation distances are:

$$\begin{cases} d_{max} = \max_j (\{d_{-180}; d_{-90}; d_0; d_{90}\}) \\ d_{avg} = \dfrac{d_{-180} + d_{-90} + d_0 + d_{90}}{4} \\ \sigma_d = \sqrt{\dfrac{(d_{-180} - d_{avg})^2 + (d_{-90} - d_{avg})^2 + (d_0 - d_{avg})^2 + (d_{90} - d_{avg})^2}{3}} \end{cases}$$

As appropriate, similar methodology can be adopted in relation to obtaining the isocentre for the patient support surface; for example, where appropriate the radiation-based methodology can be applied but using the optically obtained reference marker.

Figure 4:
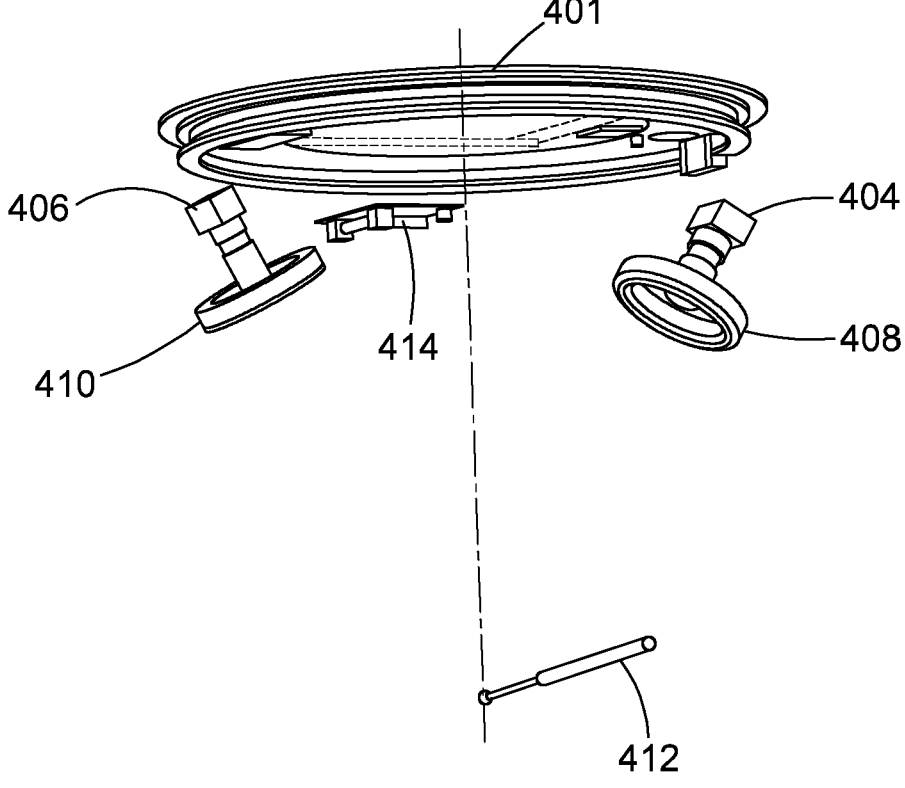
FIG. 4 depicts a dual camera optical isocentre capture apparatus according to an embodiment.

As indicated above, it is possible to rely on a single camera and two-dimensional measurements in the XY plane (effectively the horizontal plane) to identify the isocentre using optical techniques, however, if it is desired to achieve the additional resolution of isocentre identification in the Z direction this can be achieved with addition of a second camera as shown in FIG. 4. In particular, the machine head 401 includes first and second cameras 404, 406 and respective associated optics 408, 410 including a co-axial illuminator. Additionally, a ball bearing or other reference phantom is provided at 412 and additional image processing electronics and, as appropriate, an inclinometer as discussed above are provided at 414.

By using a dual camera arrangement, acquisition of 3D data is available for each measurement step using optical triangulation, and evaluation of the mechanical isocentre can be obtained in three dimensions as discussed in more detail below. Additionally, source axis distance variations (in the Z direction) can be obtained as discussed in more detail below. It will be noted that the results of the two-dimensional analysis can be relevant and applicable even when using a two camera three dimensional set up, as the two-dimensional analysis is directly comparable with analysis in operation used by Winston Lutz-like methods, in the radiation field which typically make use of a 2D sensor such an amorphous silicon detector. Of course, the availability of an additional camera according to the claimed approach provide significant additional information over conventional techniques using the actual radiation beam source. Indeed it will be seen that 3D results would not be achievable in the same manner in conventional arrangements using the actual radiation source because of the inherent absence of a second imaging source.

In order to be able to distinguish between the illumination provided corresponding to each camera, and the respective captured image, and in particular to avoid non co-axial illumination (or cross illumination) which would negatively impact accuracy, the light sources and/or interaction with the cameras can be made distinguishable. For example the IR LEDs for the respective co-axial rings can operate on different wavelengths in conjunction with tuned band pass filters for the respective cameras so that the illumination produced by the ring associated with the one camera is not detected by the other and vice versa. In an alternative approach, the IR illuminators can be pulsed in turn such that one pulses while the other is off, each being synchronised to pulse during the detection period of the respective camera such that the LEDs for the co-axial ring associated with the camera are switched on in synchronicity with the respective camera frame exposure period. Similarly, of course, the IR LED and camera will be off at the same time as well. A short (order of milliseconds) offset or gap between switching of respective cameras can be introduced to avoid the risk of stray illumination affecting the wrong camera. It will be noted that active markers can of course be used as discussed in more detail above in which case the IR illuminators are not required.

Yet further, the three-dimensional data obtained provides support of an augmented reality phase after completion of isocentre calibration. In particular a separate device such as a laptop, tablet or phone connected to the dual camera system can provide a live representation of the "beam axis" in relation to the isocentre, for example superimposed on image capture data of the device itself, by using the three-dimensional axis coordinates mapped to coordinates system of the image capture device.

In order to calibrate and identify the isocentre in a dual camera configuration, a minimal enclosing three-dimensional sphere model is applied where the image captured points form a sphere (or other three-dimensional surface) and an effective centre is derived.

This calibration method uses of a series of points at different gantry angles, calculating the position that minimize the maximum distance with the given points. This finds the minimal enclosing sphere which center is the requested isocenter position and radius is the maximum distance of the points from the isocenter.

The points are acquired for a full rotation of the gantry and at constant steps.

The points $P^b(x^b, y^b, z^b)$, acquired in the beam system at gantry angle $\theta$, are transformed into $P(x, y, z)$ in the IEC 61217 coordinate system as follows:

$$\begin{cases} x = x^b \cdot \cos\theta + z^b \cdot \sin\theta \\ y = y^b \\ z = -x^b \cdot \sin\theta + z^b \cdot \cos\theta \end{cases}$$

For each point $P_j(x_j, y_j, z_j)$ the distance from the (unknown) center $C(x_c, y_c, z_c)$ of the minimal enclosing sphere is computed:

$$d_j(x_c, y_c, z_c) = \|P_j - C\| = \sqrt{(x_j - x_c)^2 + (y_j - y_c)^2 + (z_j - z_c)^2}$$

The maximum distance of the series of point in respect to the center C is calculated:

$$D(x_c, y_c, z_c) = \max_j(d_j(x_c, y_c, z_c))$$

Finally, the radius and center of the minimal enclosing sphere is found minimizing the maximum distance $D(x_c, y_c, z_c)$:

$$R = \min_{x_c, y_c, z_c} (D(x_c, y_c, z_c))$$

It will further be seen that the claimed approach, by permitting "depth" information in Z-direction, permits accurate measurements of the source axis distance as shown in FIG. 5, in particular by deriving the isocentre position in the (x,y,z) coordinate frame. In particular the source axis distance is shown in FIG. 5 at 500 as distance between the beam source 502 and measured or calibrated isocentre 504. Once again, therefore, the use of dual cameras permits additional data and corresponding inference of relevant parameters of the device.

Referring now to FIGS. 6A-6D, an additional embodiment is described in which detection of relative rotations between a collimator and a patient support surface can be obtained making use of two reference markers, ie a dual reference marker. Referring firstly to FIGS. 6A and 6B, a side view of a linac head 600 is shown at two orthogonally spaced rotational positions and the corresponding view of a marker such as a modified ball bearing phantom 602 can be seen. In particular the ball bearing phantom comprises a rigid rod or other spacing between first and second optical markers 602a, 602b as can be seen in the rotated position of FIG. 6B. Viewing the arrangement upwardly (in the Z direction) in FIG. 6C and FIG. 6D, the corresponding rotational positions can be seen in relation to FIGS. 6A and 6B respectively.

Figure 6E:
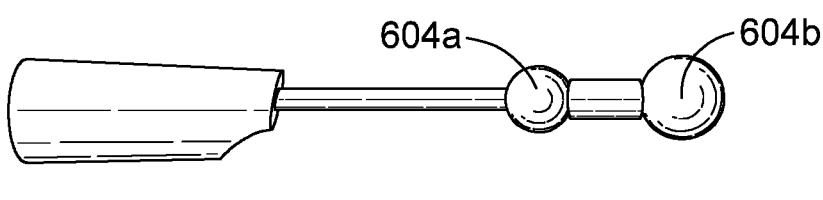

The use of a dual marker provides both continuous check of calibration and an angle detection check. As the distance between the two markers is known, the system can perform a calibration self-check continuously; for example a miscalibration arising from misalignment of one or other camera would be detected immediately by identifying an unexpected distance between the markers. Similarly, in relation to detection of relative rotation between the camera systems which are rigidly attached to the linac head, and the markers which are rigidly connected to the patient couch, as the angle can be detected and taken into account, the system can be used even at early stages of installation. In particular when the machine is not completely set up or incompletely calibrated and as a result the position of the couch and/or the head are unknown, the additional knowledge of the angle can be used at this early stage to compensate for the unknown parameters. Referring to FIG. 6E it will be seen that in some instances the respective markers can comprise spheres of different sizes which additionally can permit elimination of directional uncertainties because they easily be distinguished. It will be noted that the arrangements described with reference to FIG. 6 could equally be achieved with active markers, and that the markers could be distinguished for example by operating at different emission frequencies as required.

Operation of the arrangement will be evident to the skilled reader. In particular, using one or dual cameras and related optical reference marker or other dummy point image permits either 2D or 3D identification of isocentres for example using least squares fit techniques as described in detail above. These can be combined to obtain appropriate machine or radiation isocentre data for the radiotherapy apparatus. This can be performed in a calibration phase early in set up, even before gantry rotation and beam source are operational, ensuring that enhanced set up is provided. Of course, data can be compared against conventionally captured isocentre determination at a later phase, but additional adjustments are available prior to full configuration as a result of the claimed approach.

Figure 7:
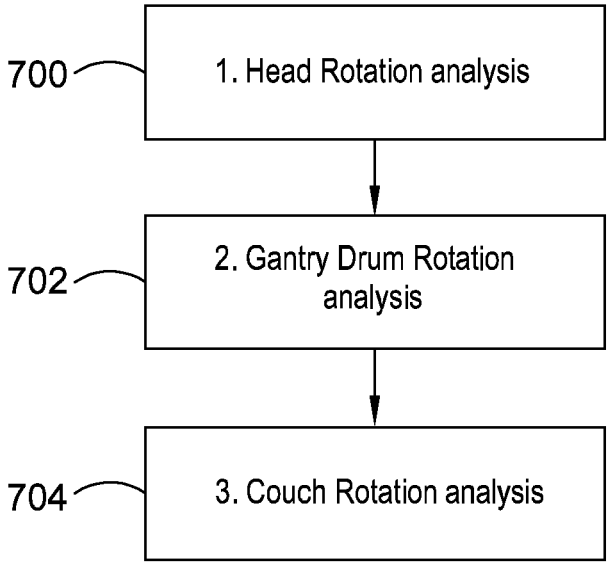
FIG. 7 depicts steps performed in implementing a method according to the present disclosure.

FIG. 7 shows in more detail the series of steps which can be performed to obtain the isocentre in the manner described above. At step 700, the axis of rotation of the collimator is determined as a result of the calibration of the collimator rotational axis procedure as discussed above. At step 702 the rotational axis of the gantry (gantry drum) and the optimum gantry isocentre are determined. At 704, the rotational axis of the couch is determined by equivalent methods to those used for the collimator. Its position is then added into the gantry isocentre calculations to permit all degrees of freedom to be taken into account when determining the isocentre.

Figure 8A:
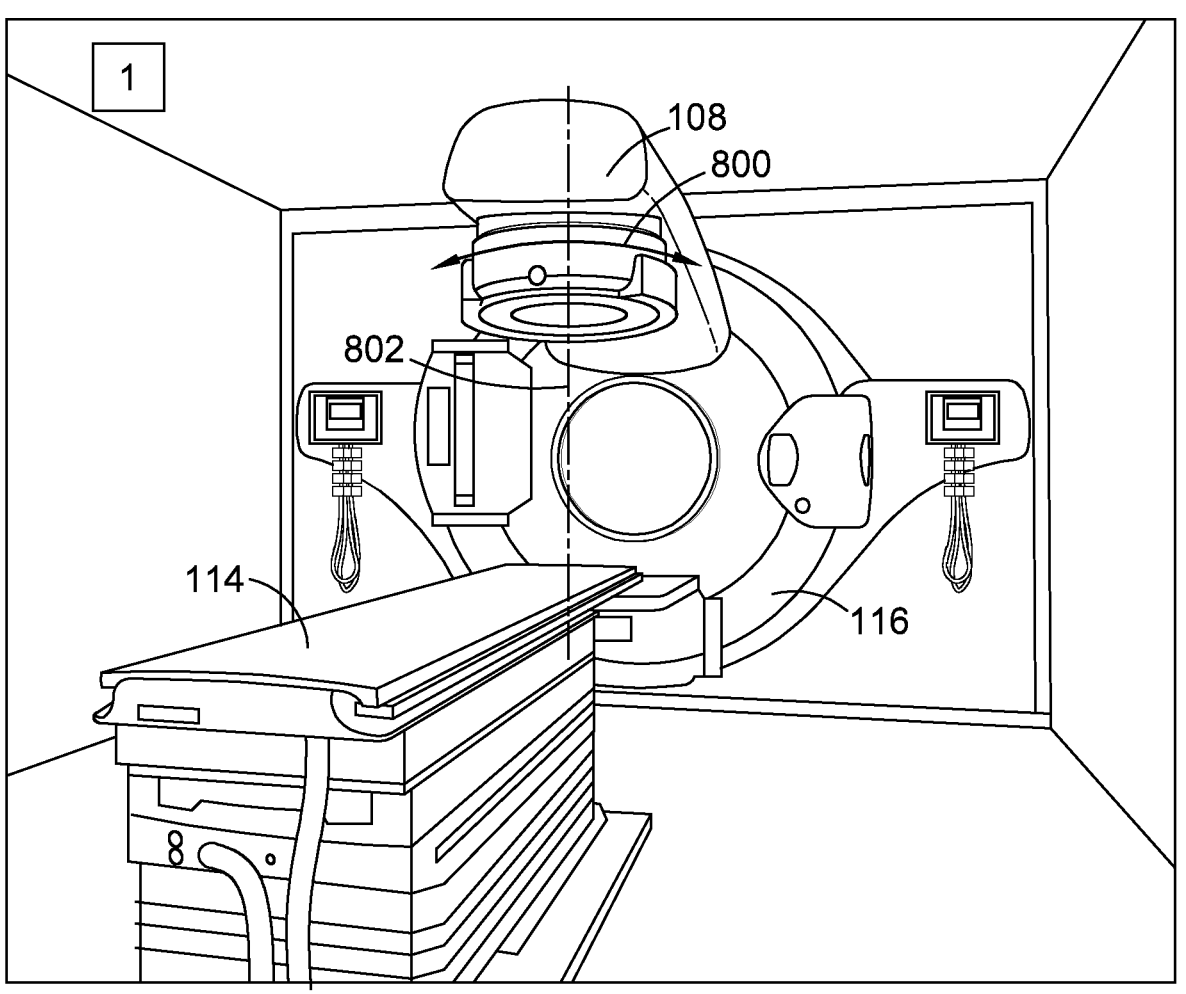
FIGS. 8A to 8C depict identification of the rotational axes in more detail.
Figure 8B:
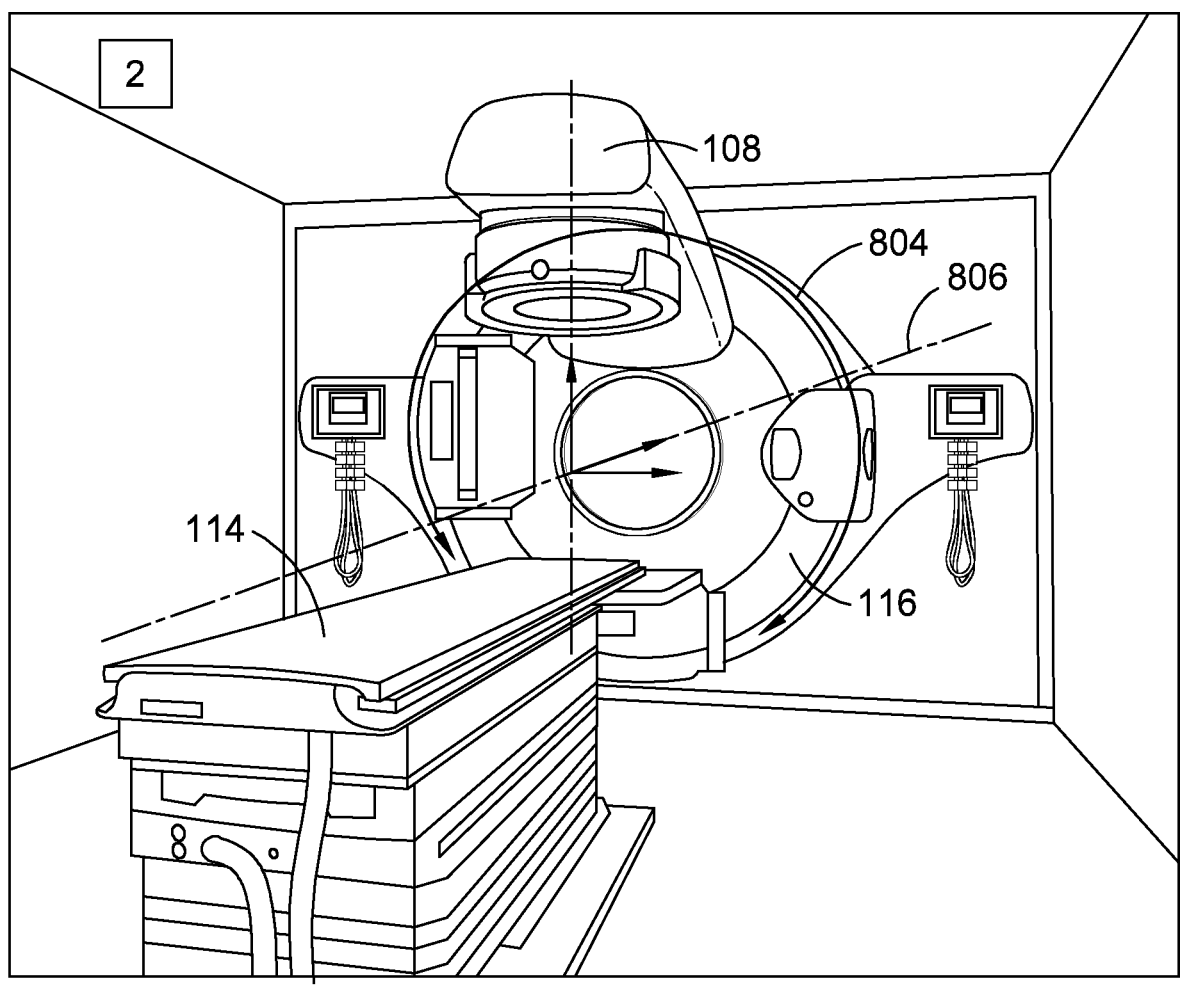
Figure 8C:
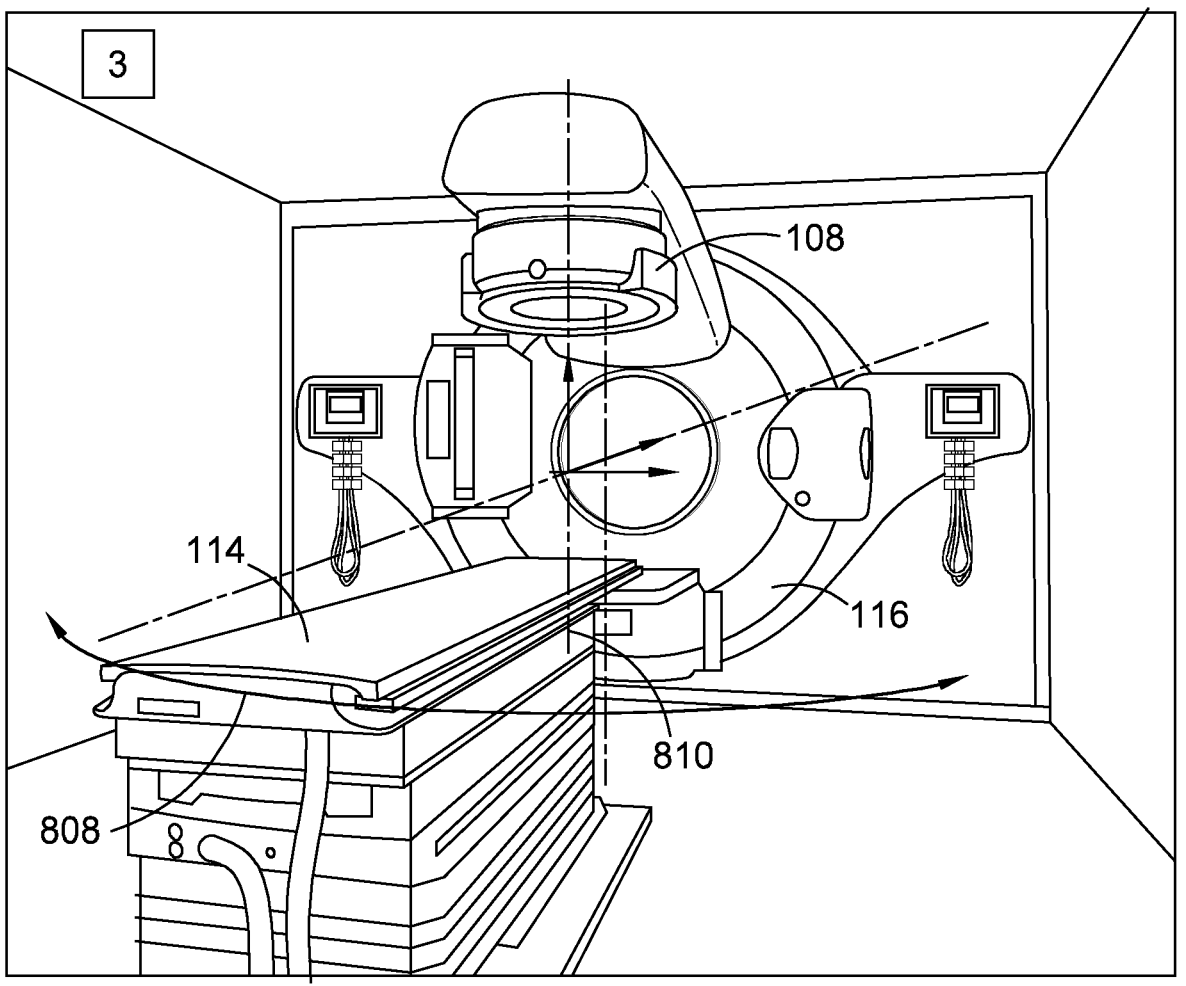

The approach can further be seen with reference to FIGS. 8A-8C where like reference numerals refer to like components. Referring to FIG. 8A the collimator head 108 rotates as shown by arrow 800 about axis 802. Referring to FIG. 8B, gantry 116 rotates as shown by arrow 804 around gantry axis 806 and as shown in FIG. 8C, patient support surface 114 rotates as shown by arrow 808 around axis 810.

The nature of the various components will be well known to the skilled person. For example, any appropriate image capture and/or illumination device can be introduced together with any appropriate dummy image point such as a ball bearing or other optical reference marker. Processing of the data for calibration, detection, and/or augmented reality representation can be performed in any appropriate manner in software, or hardware, for example by virtue of instructions stored on a computer readable medium for execution by a processor device.

The approach described can be implemented in relation to any appropriate radiotherapy device, and with any appropriate degrees of freedom including, but not limited to any combination of gantry, collimator and patient support surface. Where additional rotational or translational degrees of freedom are incorporated, calibration can nonetheless still be carried out at the pre-set up phase in the manner described above in either 2D or 3D configurations as appropriate.

It will be understood that the above description of specific embodiments is by way of example only and is not intended to limit the scope of the present disclosure. Many modifications of the described embodiments are envisaged and intended to be within the scope of the present disclosure.

For example, the provided method of identifying an isocentre of a radiotherapy apparatus can also use cameras or imaging equipment suitable for surface guided radiation therapy (SGRT) to derive the position of the dummy point. The purpose of using cameras suitable for SGRT to determine the position of the phantom or dummy point is to provide automated set-up and enhanced quality assurance (QA). Currently phantoms are manually adjusted to a required QA position using lasers/light indices to position in the intended test position. Instead it is proposed to use imaging devices or cameras that are suitable for SGRT to accurately position the phantom or dummy point before QA takes place.

SGRT is a system that comprises a pattern projector configured to project a two-dimensional (2D) or three-dimensional (3D) pattern onto a surface of an object, such as a patient positioned on a couch. In the present case the pattern project is configured to project a 2D or 3D image on the surface of a phantom or dummy. At least one detector or camera, responsive to detecting and/or imaging the projected 2D/3D pattern, is configured to generate a detection signal representative of the detected 2D/3D pattern on the object surface. The detection signal is processed by a pattern analysing circuit that is configured to generate a surface representation of at least a portion of the object surface based on the detection signal. A correction analysing circuit compares the generated surface representation with a stored reference surface representation in order to generate a correction signal. The correction signal is representative of a discrepancy in position or angle of the phantom or dummy of the surface representation relative the reference surface representation. The correction signal is further employed to generate information representing the position discrepancy. The information is then used by a processor to work out the position of the phantom and adjust the position of a phantom accordingly. A reference surface relative to the treatment isocenter position is used to calculate the necessary correction of the phantom in translational and rotational directions.

Determination of a surface representation based on detection of a projected 2D or 3D pattern onto a surface of an object is known in the art. Generally, such surface representation can be divided into feature-based representations, point-based representations, model-based representations and representations based on global shape. However, the approach of using cameras or imaging equipment suitable for SGRT to determine the position of a phantom or dummy marker is not known.

Variations in the pattern projection formed by the SGRT on the phantom along directions orthogonal to the beam axis can be derived in some embodiments from the captured image. These can be used to determine the position of the reference marker such as a ball bearing phantom (as shown by item 212 in FIG. 2). Through appropriate coordinate transformations, the measurement can be associated with the respective configuration of the radiotherapy apparatus, namely the position of the gantry, collimator and/or patient support system, and the results of the measurements can be analysed to identify shifts in the phantom's position and/or used to evaluate the accuracy of the position of the phantom.

As previously described in relation to radiation isocenter derivation, an image capture device can be a digital camera or other suitable device mounted to the radiotherapy apparatus. The dummy point location can then be derived from the captured imaging or camera data, for example by extrapolating the dummy's position based on the readings 2D and 3D patterns. In optional embodiments, by using two or more image capture devices additional 3D information can be obtained permitting yet further accuracy. Accordingly, machine set up and calibration can be improved with efficiency and accuracy of the location of the dummy point or phantom can be significantly enhanced.

Cameras used for SGRT are already present in the radiotherapy room to provide patient position couch adjustment and to identify patient orientation and alignment. The same system can also be used to identify relative position of a phantom. For example, a ball bearing can be used because the dimensions and other parameters of a ball bearing are already known. This means that no extra equipment is required in the radiotherapy room to ensure accurate determination of the position of the phantom or dummy point. The position of the dummy point or phantom can be compared to a desired position, and feed couch adjustment instructions to move couch to position phantom in desired position relative to machine. This provides an automated set up of the phantom and the position of the phantom can be more accurately provided. In turn this allows a more accurate reading of the radiation isocenter to be performed.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A method of identifying an isocentre of a radiotherapy apparatus, the method comprising:
   capturing an illumination of respective dummy point images of respective dummy points at respective rotational positions of a component of the radiotherapy apparatus at an image capture device mounted on the radiotherapy apparatus;
   deriving the isocentre from the captured respective dummy point images, wherein an individual dummy point of the dummy points comprises an active marker, wherein a first dummy point and a second spaced dummy point are distinguishable by at least one of a size or an optical characteristic detectable by optical equipment without requiring issuing therapeutic radiation.

2. The method as claimed in claim 1, wherein an individual dummy point comprises a point fixed in relation to a space including the radiotherapy apparatus.

3. The method as claimed in claim 1, wherein the active marker comprises an illumination source.

4. The method as claimed in claim 3, wherein the illumination source comprises an infrared (IR) LED.

5. The method as claimed in claim 1, the dummy points comprising a first dummy point and a second spaced dummy point that is spaced apart from the first dummy point.

6. The method as claimed in claim 5, wherein the first dummy point is spaced apart from the second spaced dummy point so as to be distinguishable, using the image capture device, from the second spaced dummy point.

7. The method as claimed in claim 1, wherein the image capture device comprises a camera mounted on a radiotherapy apparatus gantry.

8. The method as claimed in claim 1, wherein the image capture device comprises a camera, further comprising:
   a ring illuminator located parallel to or co-axial with optics of the camera.

9. The method as claimed in claim 1, wherein the image capture device is a first image capture device, the method further comprising:
   capturing the respective dummy point images at, respectively, the first image capture device and a second image capture device.

10. The method as claimed in claim 9 further comprising:
   controlling at least one of the respective first and second image capture devices and respective illumination sources to distinguish the captured respective dummy point images captured at each device.

11. The method as claimed in claim 10, wherein the respective illumination sources emit radiation tuned to respective image capture devices.

12. The method as claimed in claim 10, wherein the respective illumination sources emit radiation timed to respective image capture devices.

13. The method as claimed in claim 9 further comprising:
   storing virtual or augmented reality representation data for visualization of the isocentre.

14. The method as claimed in claim 9, further comprising:
   capturing source-axis distance data based on the captured respective dummy point images.

15. The method of claim 1, further comprising:
   determining a position of a dummy point in the respective dummy point images using an imaging equipment of a surface guided radiation therapy system of the radiotherapy apparatus.

16. A non-transitory computer readable medium comprising instructions which, when executed by a processor, cause the processor to perform a method of identifying an isocentre of a radiotherapy apparatus, the method comprising:
   capturing an illumination of respective dummy point images of respective dummy points at respective rotational positions of a component of the radiotherapy apparatus at an image capture device mounted on the radiotherapy apparatus; and
   deriving the isocentre from the captured respective dummy point images, wherein the respective dummy points comprise respective active markers, and wherein a first dummy point and second spaced dummy point are distinguishable by at least one of a size or an optical characteristic detectable by optical equipment without requiring issuing therapeutic radiation.

17. A radiotherapy apparatus comprising:
   an image capture device for capturing isocentre identification data, wherein the radiotherapy apparatus is configured to perform a method of identifying an isocentre of the radiotherapy apparatus, the method comprising:
   capturing an illumination of respective dummy point images of respective dummy points located at respective rotational positions of a component of the radio-
therapy apparatus at the image capture device mounted
on the radiotherapy apparatus; and deriving the isocentre from the captured respective
dummy point images, wherein the respective dummy
points comprise respective active markers, and wherein
a first dummy point and a second spaced dummy point
are distinguishable by at least one of a size or an optical
characteristic detectable by optical equipment without
requiring issuing therapeutic radiation.

\* \* \* \* \*